United States Patent
Kim et al.

(10) Patent No.: US 11,111,203 B2
(45) Date of Patent: Sep. 7, 2021

(54) SYSTEM AND METHOD FOR MANUFACTURING ESTER-BASED COMPOSITION

(71) Applicant: LG CHEM, LTD., Seoul (KR)

(72) Inventors: Hyun Kyu Kim, Daejeon (KR); Sung Kyu Lee, Daejeon (KR); Jeong Ju Moon, Daejeon (KR); Hyoung Jun, Daejeon (KR); Chan Hyu Jin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 16/838,593

(22) Filed: Apr. 2, 2020

(65) Prior Publication Data

US 2020/0317600 A1    Oct. 8, 2020

(30) Foreign Application Priority Data

Apr. 4, 2019 (KR) .................. 10-2019-0039716
Mar. 30, 2020 (KR) .................. 10-2020-0038458

(51) Int. Cl.
*B01J 19/24* (2006.01)
*B01J 4/00* (2006.01)
(Continued)

(52) U.S. Cl.
CPC ............ *C07C 67/08* (2013.01); *B01D 3/14* (2013.01); *B01J 4/008* (2013.01); *B01J 19/0053* (2013.01); *B01J 19/2445* (2013.01); *B01J 31/12* (2013.01); *C07C 67/48* (2013.01); *B01J 2204/002* (2013.01); *B01J 2219/00031* (2013.01);
(Continued)

(58) Field of Classification Search
CPC .............. B01J 19/2445; B01J 19/245; B01J 2219/00164; B01J 2219/0031; B01J 2219/0038; B01J 4/008; B01J 4/02
See application file for complete search history.

(56) References Cited

U.S. PATENT DOCUMENTS 3,780,135 A * 12/1973 Perry .................... C08F 2/38
                                                       525/323
5,264,315 A * 11/1993 Tan .................... B01J 19/1862
                                                       430/110.2
(Continued)

FOREIGN PATENT DOCUMENTS

JP    2009-114273 A    5/2009
JP    2009-191205 A    8/2009
(Continued)

OTHER PUBLICATIONS

Mustafizur Rahman et al., "The plasticizer market: an assessment of traditional plasticizers and research trends to meet new challenges", Progress in Polymer Science, 2004, 29, pp. 1223-1248.
(Continued)

*Primary Examiner* — Lessanework Seifu
(74) *Attorney, Agent, or Firm* — Dentons US LLP (57) ABSTRACT

The present disclosure relates to a method and a system for manufacturing an ester-based composition which are characterized in sequentially operating a plurality of batch reactors, and since an ester-based composition is semi-continuously manufactured, the productivity is high and the stability of a batch reactor is secured.

7 Claims, 3 Drawing Sheets

(51) Int. Cl.
    *C07C 67/08*     (2006.01)
    *B01J 19/00*     (2006.01)
    *B01J 31/12*     (2006.01)
    *C07C 67/48*     (2006.01)
    *B01D 3/14*     (2006.01)

(52) U.S. Cl.
    CPC ............ *B01J 2219/00038* (2013.01); *B01J 2219/00164* (2013.01); *B01J 2231/49* (2013.01); *B01J 2531/46* (2013.01)

(56) References Cited

U.S. PATENT DOCUMENTS

| | | | |
|---|---|---|---|
| 5,282,680 A * | 2/1994 | Amano | B01F 5/16 366/266 |
| 8,410,306 B2 * | 4/2013 | Bauduin | C07C 67/08 560/190 |
| 2007/0077635 A1 | 4/2007 | Brunner et al. | |
| 2019/0263745 A1 | 8/2019 | Lee et al. | |

FOREIGN PATENT DOCUMENTS

| | | |
|---|---|---|
| KR | 10-2013-0042742 A | 4/2013 |
| KR | 10-1354141 B | 1/2014 |
| KR | 10-1663586 B1 | 10/2016 |
| KR | 10-2019-0027623 A | 3/2019 |

OTHER PUBLICATIONS

Nadeem Rezaq Janjua et al., "Systemic Uptake of Diethyl Phthalate, Dibutyl Phthalate and Butyl Paraben Following Whole-Body Topical Application and Reproductive and Thyroid Hormone Levels in Humans", Environmental Science and Technology, 2007, 41, pp. 5564-5570.

* cited by examiner

SYSTEM AND METHOD FOR MANUFACTURING ESTER-BASED COMPOSITION

CROSS-REFERENCE TO RELATED APPLICATIONS

This application claims the benefit of and priority to Korean Application No. 10-2019-0039716, filed on Apr. 4, 2019, and Korean Application No. 10-2020-0038458, filed on Mar. 30, 2020, all of which are hereby incorporated by reference in their entirety for all purposes as if fully set forth herein.

TECHNICAL FIELD

The present invention relates to a method and a system for manufacturing an ester-based composition which are characterized in sequentially operating a plurality of batch reactors.

BACKGROUND ART

Phthalate-based plasticizers had occupied 92% of the world's plasticizer market by the 20th century (Mustafizur Rahman and Christopher S. Brazel "The plasticizer market: an assessment of traditional plasticizers and research trends to meet new challenges" Progress in Polymer Science 2004, 29, 1223-1248), and are additives used to improve the processability of polyvinyl chloride (hereinafter, referred to as PVC) by imparting flexibility, durability, cold resistance, and the like and lowering viscosity during melting. Phthalate-based plasticizers are introduced into PVC in various contents and used not only for hard products such as rigid pipes, but also for soft products such as food packaging materials, blood bags, and flooring materials since the phthalate-based plasticizers are soft and stretchable. Thus, the phthalate-based plasticizers are more closely related to real life than any other materials and are widely used for materials which come into direct contact with a human body.

However, despite the compatibility with PVC and excellent softness imparting properties of phthalate-based plasticizers, there has been controversy over the harmful nature of the phthalate-based plasticizers in that when a PVC product containing a phthalate-based plasticizer is used in real life, the phthalate-based plasticizer may be leaked little by little out of the product and act as a suspected endocrine disruptor (environmental hormone) and a carcinogen to the level of a heavy metal (N R Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570). Particularly, since a report was published in the 1960s in the United States that diethylhexyl phthalate (di-(2-ethylhexyl) phthalate, DEHP), the most used phthalate plasticizer, leaked out of PVC products, global environmental regulations have started to be implemented in addition to various studies on the harmful nature of the phthalate-based plasticizer on human bodies, boosted by increasing interest in environmental hormones in the 1990s.

Thus, in order to respond to environmental hormonal problems and environmental regulations due to the leakage of phthalate-based plasticizers, many researchers have been conducting research in order to develop a new non-phthalate-based alternative plasticizer without phthalic anhydride used in the manufacturing of phthalate-based plasticizers, or to develop a leakage suppression technology which suppresses the leakage of phthalate-based plasticizers, thereby significantly reducing risks to human bodies and which meets environmental standards.

Meanwhile, as non-phthalate-based plasticizers, terephthalate-based plasticizers not only have an equivalent level of physical properties with phthalate-based plasticizers, but also have been spotlighted as a material free from environmental problems, so that various types of terephthalate-based plasticizers have been developed. In addition, research on developing terephthalate-based plasticizers with excellent physical properties as well as research on equipment for manufacturing such terephthalate-based plasticizers have been actively conducted, and there has been a demand for more efficient, more economical and simpler process designs in terms of process design.

PRIOR ART DOCUMENT (Patent Document 1) Korean Patent Laid-Open Publication No. 10-1354141

(Non-patent Document 1) Mustafizur Rahman and Christopher S. Brazel "The plasticizer market: an assessment of traditional plasticizers and research trends to meet new challenges" Progress in Polymer Science 2004, 29, 1223-1248

(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

An aspect of the present invention provides an efficient method and an efficient system for manufacturing an ester-based composition, the method and the system securing the stability of batch reactors and the efficiency of a semi-continuous process by employing a plurality of batch reactors mainly used in an esterification reaction, connecting the plurality of batch reactors in parallel, and sequentially operating the same such that the entire process is operated semi-continuously.

Technical Solution

According to an aspect of the present invention, there is provided a method for manufacturing an ester-based composition, the method including a step S1 of injecting a polycarboxylic acid and a first alcohol having 3 to 10 alkyl carbon atoms into a mixer to form a reaction mixture, a step S2 of sequentially injecting the reaction mixture into N number of batch reactors to perform a reaction such that the reaction is sequentially completed in the N number of batch reactors to semi-continuously manufacture reaction products, and a step S3 of semi-continuously moving the reaction products into a separation unit to remove unreacted alcohol, wherein N is an integer of 3 or greater.

According to another aspect of the present invention, there is provided a system for manufacturing an ester-based composition, the system including a mixer in which a reaction mixture of a polycarboxylic acid and a first alcohol having 3 to 10 alkyl carbon atoms is formed, a reaction unit provided with N number of batch reactors connected in parallel in which an esterification reaction of the reaction mixture is performed and with an outlet line for discharging reaction products from the N number of batch reactors, a supply control unit for controlling the injection amount and the injection path of the reaction mixture such that the reaction mixture is sequentially supplied to the N number of batch reactors from the mixer to allow the reaction to be sequentially completed, and a separation unit for receiving the reaction products and removing unreacted alcohol therefrom, the separating unit including one or more separation columns.

Advantageous Effects

A manufacturing method and a manufacturing system of the present invention allow a plurality of batch reactors connected in parallel to be sequentially driven such that an entire reaction process is operated semi-continuously, so that it is possible to secure both the stability of a batch reactor and the efficiency of a semi-continuous process.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

In a manufacturing method and a manufacturing system of the present invention, a polycarboxylic acid refers to a compound having two or more carboxylic acid groups, for example, a dicarboxylic acid, a tricarboxylic acid, or a tetracarboxylic acid. A polycarboxylic acid used in the present invention may have 2 to 5 carboxylic acid groups, 2 to 4 carboxylic acid groups, or 2 to 3 carboxylic acid groups. When a polycarboxylic acid has too many carboxylic acid groups, it may not easy to apply the polycarboxylic acid to the manufacturing method or the manufacturing system of the present invention due to a high molecular weight of the polycarboxylic acid itself. The polycarboxylic acid is preferably a dicarboxylic acid, a tricarboxylic acid, or a tetracarboxylic acid. The dicarboxylic acid may be one or more selected from the group consisting of a linear dicarboxylic acid having 2 to 10 carbon atoms, a terephthalic acid, a phthalic acid, an isophthalic acid, and a cyclohexane dicarboxylic acid, and the tricarboxylic acid may be one or more selected from the group consisting of a citric acid, a trimellitate acid, and a cyclohexane tricarboxylic acid. The tetracarboxylic acid may be one or more selected from the group consisting of a benzenetetracarboxylic acid, a furantetracarboxylic acid, a cyclohexane tetracarboxylic acid, and a tetrahydrofuran tetracarboxylic acid. In addition, the polycarboxylic acid may not only include itself, but also include an anhydride or a derivative thereof.

In the manufacturing method and the manufacturing system of the present invention, it is preferable that the (first/second) alcohol having 3 to 10 alkyl carbon atoms is one or more selected from the group consisting of propanol, butanol, pentanol, hexanol, heptanol, octanol, nonanol and decanol, all of which are of a linear type or a branched type. In addition, the alcohol may be alcohol of a single type, or may be in the form of a mixture containing isomers having the same number of carbon atoms. For example, when the alcohol is alcohol having 3 alkyl carbon atoms, the alcohol may be 1-propanol or 2-propanol, or may be in the form of a mixture containing 1-propanol and 2-propanol in a predetermined ratio. When the alcohol is in the form of a mixture containing isomers having the same number of carbon number, the relative amount of each isomer is not particularly limited.

System for Manufacturing Ester-Based Composition

The present invention provides a system for manufacturing an ester-based composition, the system including a mixer in which a reaction mixture of a polycarboxylic acid and a first alcohol having 3 to 10 alkyl carbon atoms is formed, a reaction unit provided with N number of batch reactors connected in parallel in which an esterification reaction of the reaction mixture is performed, an inlet line for receiving the reaction mixture from the mixer, and an outlet line for discharging reaction products from the N number of batch reactors, a supply control unit for controlling the injection amount and the injection path of the reaction mixture such that the reaction mixture is sequentially supplied to the N number of batch reactors from the mixer to allow the reaction to be sequentially completed, and a separation unit for receiving the reaction products through the outlet line of the reaction unit and removing unreacted alcohol therefrom.

The manufacturing system provided by the present invention is a system to be used for executing a manufacturing method of the present invention and includes a mixer 1, a supply control unit 2, a reaction unit 3, and a separation unit 4.

Figure 1:
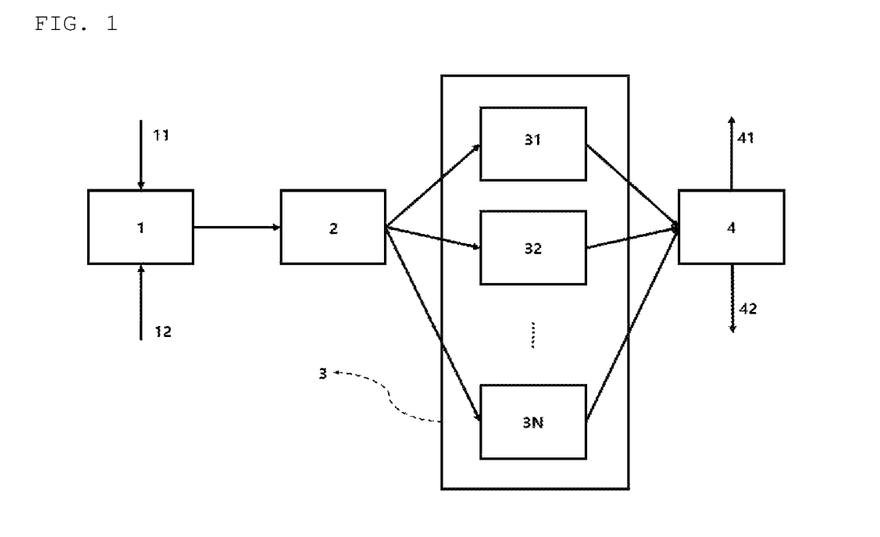
FIG. 1 is a process flow diagram illustrating a system for manufacturing an ester-based composition including a mixer, a supply control unit, a reaction unit, and a separation unit according to an embodiment of the present invention.

As shown in FIG. 1, the mixer 1 performs the mixing of a polycarboxylic acid 11 and a first alcohol 12 injected into the mixer, and a reaction mixture generated from the mixer passes through the supply control unit 2 to be sequentially injected into each of batch reactors 31 to 3N included in the reaction unit 3. When a reaction is completed in each reactor, reaction products are moved to the separation unit 4, and in the separation unit, unreacted alcohol 42 is removed and an ester-based composition 41 is finally obtained.

Particularly, the supply control unit 2 included in the manufacturing system of the present invention serves to determine when to start an injection, how much to inject, and when to complete the injection for each reactor when the reaction mixture is sequentially injected into each reactor from the mixer, thereby enabling the sequential injection of the reaction mixture into each reactor connected in parallel and the discharge of the reaction products.

Figure 2:
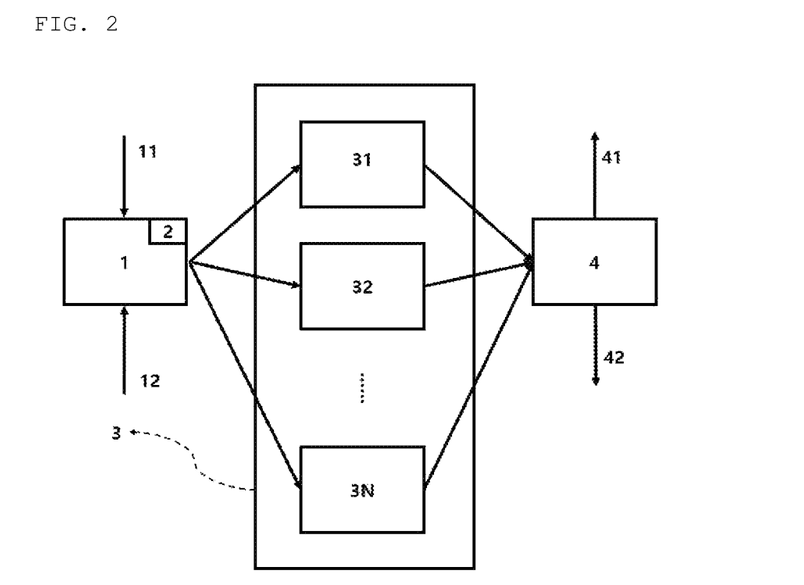
FIG. 2 is a process flow diagram illustrating a system for manufacturing an ester-based composition including a mixer, a supply control unit, a reaction unit, and a separation unit according to an embodiment of the present invention, wherein the supply control unit is provided inside the mixer.

The supply control unit may be a separate unit connected to the mixer as shown in FIG. 1, and may be a unit included in the mixer as shown in FIG. 2. When the supply control unit is included in the mixer, the supply control unit may control the injection path and the injection amount of the reaction mixture directly discharged from the mixer.

Figure 3:
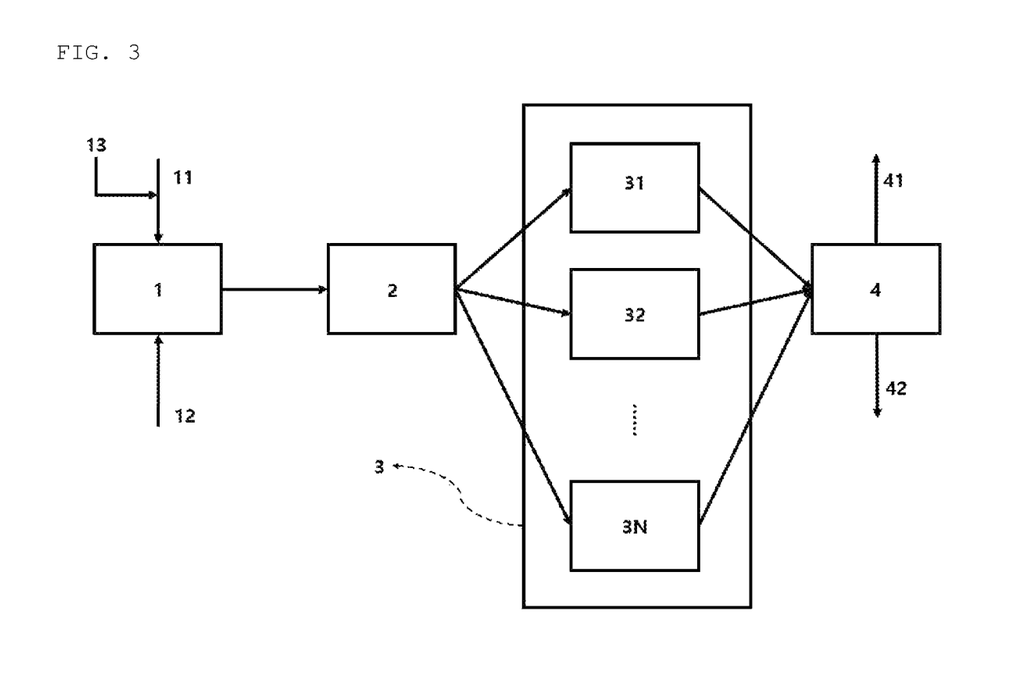
FIGS. 3-5 are process flow diagrams each illustrating a system for manufacturing an ester-based composition indicating a path in which a catalyst may be injected, in one embodiment of the present invention.
Figure 4:
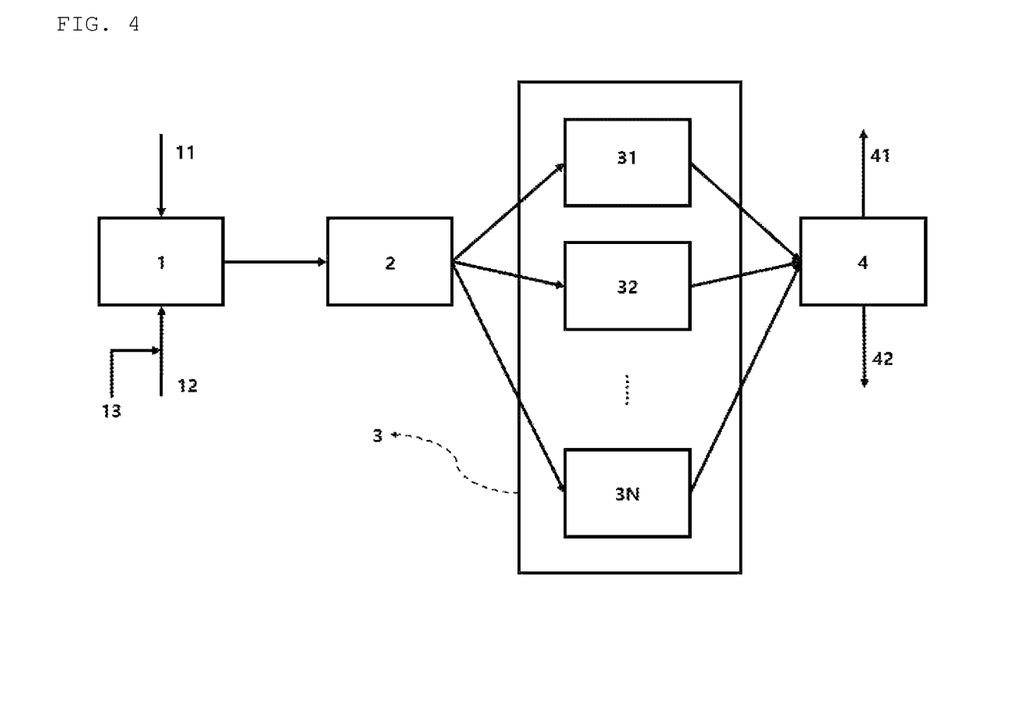
Figure 5:
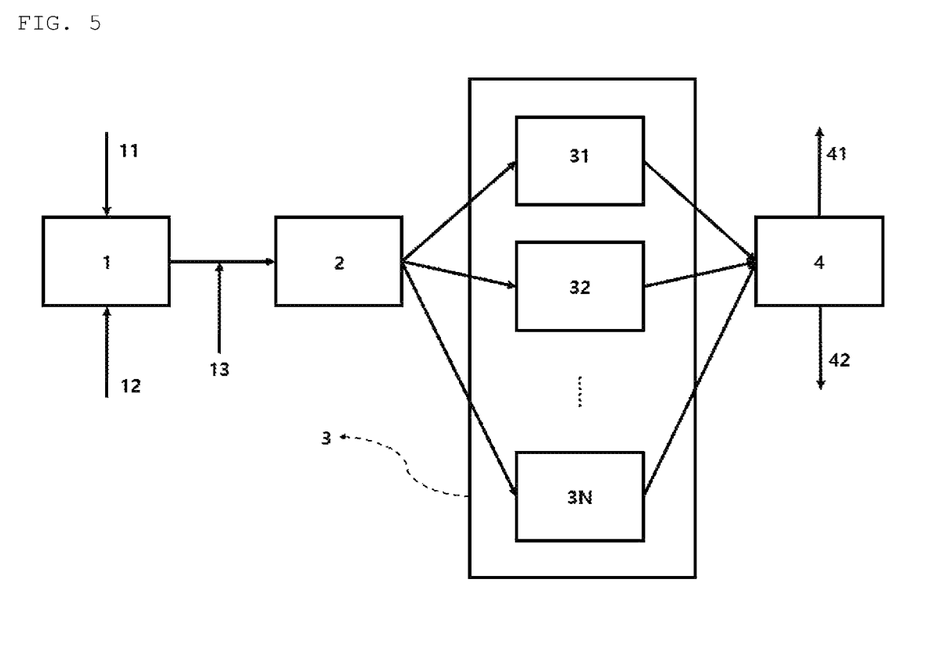

Also, as shown in FIG. 3, FIG. 4, or FIG. 5, in the manufacturing system of the present invention, a catalyst 13 may be injected into the polycarboxylic acid, the first alcohol, or the reaction mixture thereof.

Figure 6:
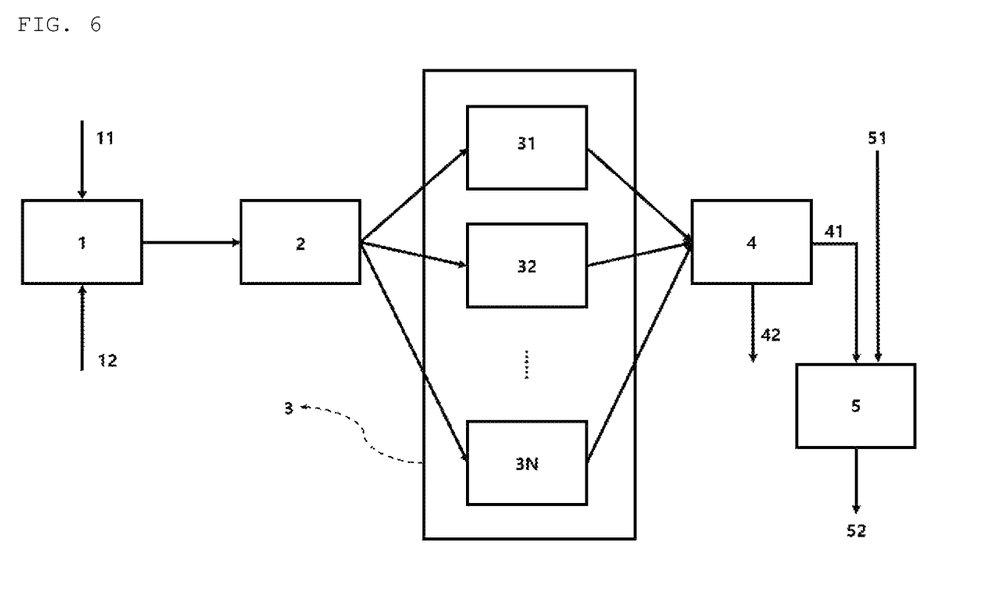
FIG. 6 is a process flow diagram illustrating a system for manufacturing an ester-based composition including a mixer, a supply control unit, a reaction unit, a separation unit, and a trans-reaction unit according to an embodiment of the present invention.

As shown in FIG. 6, the manufacturing system of the present invention may further include a trans-reaction unit 5 for performing a trans-esterification reaction by adding a second alcohol having 3 to 10 alkyl carbon atoms to the reaction products from which the unreacted alcohol has been removed. The second alcohol 52 injected from the trans-reaction unit is different from the first alcohol injected from the mixer, and may pass through the trans-reaction unit to manufacture an ester-based composition 51 including different ester-based compounds.

In addition, in the manufacturing system provided by the present invention, at least one among the N number of reactors may be provided with a gas-liquid separation column connected to an upper portion of the reactor and separating alcohol and water discharged through the upper portion of the reactor, a condenser for cooling a gas discharged through an upper line of the gas-liquid separation column, and a decanter for separating a liquid discharged through a lower line of the gas-liquid separation column and a liquid condensed in the condenser into different layers and recirculating the alcohol into the reactor.

As described above, when the reactor is provided with the gas-liquid separation column, the condenser, and the decanter, it is possible to increase the efficiency and economic feasibility of the reaction by re-liquefying alcohol vaporized during the reaction and re-injecting the re-liquefied alcohol into the reactor, and at the same time, it is possible to allow the reaction to proceed towards a forward reaction by removing water, which is a by-product of an esterification reaction, that is, allowing a high conversion rate to be achieved.

Also, the supply control unit in the manufacturing system provided by the present invention may control one or more selected from the injection path and the injection flow rate of the reaction mixture to be changed according a predetermined time interval.

The supply control unit in the manufacturing system of the present invention should determine the injection path and the injection flow rate of the reaction mixture such that N number of reactors may operate sequentially and set a time interval which is determined in consideration of the reaction duration, the total number of reactors, and the desired production amount, and the like. If the injection path and the injection flow rate of the reaction mixture is controlled at the predetermined time interval, at the time when the reaction products are all or almost discharged after the reaction is completed in each reactor, the reaction mixture is started to be injected back into a corresponding reactor, so that all of the reactors may be operated without being stopped, and the efficiency of the process may be increased.

In addition, the time interval set in the supply control unit may be 50%, 60%, 70%, 80%, 90% or greater, or 150%, 140%, 130%, 120%, 110% or less of a value obtained by dividing the reaction duration in one reactor by N. When the time interval is set in the above-described range, It is possible to minimize the loss of reactors not operating.

Meanwhile, the above-described reaction duration is a sum of the amount of time consumed for the reaction and the amount of time consumed for the injection of the reaction mixture and the discharge of the reaction products. For example, when 30 minutes are consumed for the reaction, and 15 minutes are consumed for each of the injection of the reaction mixture and the discharge of the reaction products, the reaction duration is 60 minutes. In this case, if there are four reactors, the injection time interval for each reactor is 15 minutes, so that the reaction mixture is injected into each reactor every 15 minutes.

Method for Manufacturing Ester-Based Composition

The present invention provides a method for manufacturing an ester-based composition, the method including a step S1 of injecting a polycarboxylic acid and a first alcohol having 3 to 10 alkyl carbon atoms into a mixer to form a reaction mixture, a step S2 of sequentially injecting the reaction mixture into N number of batch reactors to perform a reaction such that the reaction is sequentially completed in the N number of batch reactors to semi-continuously manufacture reaction products, and a step S3 of semi-continuously moving the reaction products into a separation unit to remove unreacted alcohol, wherein N is an integer of 3 or greater.

Mixing Step (S1)

The manufacturing method of the present invention includes the step S1 of injecting a polycarboxylic acid and a first alcohol having 3 to 10 alkyl carbon atoms into a mixer to form a reaction mixture.

Specifically, the step S1 for forming the reaction mixture is a step of uniformly mixing the polycarboxylic acid and the first alcohol having 3 to 10 carbon atoms in the mixer. In the present step, before the polycarboxylic acid and the first alcohol having 3 to 10 carbon atoms, which correspond to reaction raw materials, are injected into a reactor, the polycarboxylic acid and the first alcohol having 3 to 10 carbon atoms are uniformly pre-mixed in the mixer, so that it is possible to solve a non-uniform reaction which may occur when the raw materials are directly injected into the reactor. Particularly, since the reactor used in the present invention is a batch reactor, when reaction raw materials are not pre-mixed before being injected into the reactor, depending on a position inside the reactor, the non-uniformity of the raw materials may be greatly increased, and when stirring is performed poorly inside the reactor, some raw materials may be accumulated in particular, and thus, it may be difficult to secure uniform reaction duration and a uniform conversion rate. However, when reaction raw materials are pre-mixed and then injected, it is possible to obtain a substantially uniform reaction degree over the entire region of the reactor, and the reaction rate of each reactor may be maintained to be substantially uniform to secure the stability of the entire process.

In the manufacturing method of the present invention, the step S1 may further include a step in which the reaction mixture is heated to 50-200° C., preferably 60-190° C., more preferably 70-180° C. Since the reaction mixture is heated in the step S2 after the step S1 and then subjected to a reaction, when the reaction mixture is pre-heated and then injected into a reactor, the reaction mixture may be reacted easily and fast in the reactor. However, if an elevated temperature in the step S1 is too low, the effect of pre-heating before injection is poor. If heated to an excessively high temperature and injected into a reactor, the polycarboxylic acid and the first alcohol having 3 to 10 alkyl carbon atoms are vaporized and the like, so that a uniform reaction may not rather proceed.
Reaction Step (S2)

The method for manufacturing an ester-based composition of the present invention includes the step S2 of sequentially injecting the reaction mixture into N number of batch reactors to perform a reaction such that the reaction is sequentially completed in the N number of batch reactors to semi-continuously manufacture reaction products.

In the case of a reaction process in which a typical batch reactor is used, although a large amount of reaction products could be stably manufactured at one time, the reactor is not operated during a process in which reaction raw materials are injected or the reaction products are discharged, so that there is a disadvantage in terms of the efficiency of the entire process. Therefore, the present inventors have invented a method for manufacturing an ester-based composition, the method in which a plurality of batch reactors are sequentially used, so that reaction products are semi-continuously manufactured while the stability of the batch reactor is still maintained.

Specifically, in the step S2 of the manufacturing method of the present invention, the reaction mixture is sequentially injected into the N number of batch reactors, and each reactor into which the reaction mixture is injected is heated to complete a reaction. After the reaction is completed, each reactor also sequentially discharges reaction products.

For example, the step S2 may be performed in the following manner:

1) A reaction mixture uniformly mixed in a mixer is injected into a first reactor, and after a predetermined amount of the reaction mixture is injected into the first reactor, the injection is stopped.

2) After the injection is stopped, the first reactor is heated to perform a reaction, and the mixer injects the reaction mixture into a second reactor.

3) After a predetermined amount of the reaction mixture is injected into the second reactor, the injection is stopped. After this point, the second reactor is heated to perform a reaction, and the mixer injects the reaction mixture into a third reactor.

4) N number of reactors sequentially manufacture reaction products in the above manner, and after the reaction mixture is injected into an N-th reactor, the reaction mixture is injected back into the first reactor. Also, reaction products manufactured after the reaction is completed are sequentially discharged in the same manner.

In the step S2, a time interval between the injection into each reactor, that is, a time interval of the sequential injection is 90% to 110%, preferably 100% of a value obtained by dividing the total reaction duration by the number of reactors. When the reaction mixture is injected into each reactor at the above interval, at the time when the reaction products are all or almost discharged after the reaction is completed in each reactor, the reaction mixture is started to be injected back into a corresponding reactor, so that all of the reactors may be operated without being stopped and the efficiency of the process may be increased.

The above-described reaction duration is a sum of the amount of time consumed for the reaction and the amount of time consumed for the injection of the reaction mixture and the discharge of the reaction products. For example, when 30 minutes are consumed for the reaction, and 15 minutes are consumed for each of the injection of the reaction mixture and the discharge of the reaction products, the reaction duration is 60 minutes. In this case, if there are four reactors, the injection time interval for each reactor is 15 minutes, so that the reaction mixture is injected into each reactor every 15 minutes.

In the manufacturing method of the present invention, in the step S2, the injection of the reaction mixture into a reactor, heating, a reaction, and the discharge of reaction products are all performed at the same time, so that at least one of a plurality of reactors should receive the reaction mixture, at least another one of the plurality of reactors should perform the reaction, and at least another one of the plurality of reactors should discharge the reaction products. Therefore, N is preferably an integer of 3 or greater.

Particularly, N may be an integer of 3 to 10, an integer of 3 to 7, or an integer of 3 to 5. If there are too many reactors, a variety of additional apparatuses are needed, including a control unit for controlling a reaction mixture to be injected into each reactor in order and reaction products to be discharged from each reactor. Furthermore, reaction duration per one reactor may be shorter than the sum of the amount of injection time of the raw materials injected into a reactor and the amount of discharge time of a reaction products, so that there may be time during which the reactor does not operate before receiving raw materials, which may result in adverse effects on productivity. In addition, the space required for the placement of each reactor becomes also excessive, which may be inefficient in terms of the costs for the entire process.

In the step S2 of the manufacturing method of the present invention, an esterification reaction of the polycarboxylic acid and the first alcohol having 3 to 10 alkyl carbon atoms is performed. An esterification reaction refers to a reaction which a hydroxy group of first alcohol and a carboxylic acid group of a polycarboxylic acid are reacted, thereby forming an ester bond. The esterification reaction of the step S2 may be performed at 130-250° C., preferably 140-240° C., more preferably 150-230° C. When an elevated temperature in the step S2 is lower than the above range, energy required for the reaction is not sufficiently supplied, so that the reaction may not proceed to a sufficient degree. When higher than the above range, vaporization of reaction mixture components, or the like occurs during the reaction as in the step S1, and thus, reaction products may not be manufactured to a sufficient amount.

Separation Step (S3)

The manufacturing method of the present invention includes the step S3 of semi-continuously moving the reaction products into a separation unit to remove unreacted alcohol.

Specifically, in the step S3, reaction products manufactured in each of the N number of batch reactors are semi-continuously moved to a separation unit, and then, unreacted alcohol is removed in the separation unit. As described above, as the injection of the reaction mixture into the N number of batch reactors may be sequentially performed, the discharge of the reaction products manufactured in each reactor may be also sequentially, or semi-continuously, performed.

The separation unit used in the step S3 may include one or more separation columns. Depending on the number of stages of the separation column included in the separation unit in the manufacturing method of the present invention, the composition ratio of a composition to be finally manufactured may vary. Those skilled in the art may appropriately adjust the number of stages of the separation column included in the separation unit according to the composition ratio or properties of the composition to be manufactured. In addition, the separation unit may include a purification tank of a drum type in addition to the separation column. The separation unit may remove the amount of unreacted alcohol included in the reaction products to a level of 30% or less, preferably 20% or less, more preferably 10% or less of the total. Since the unreacted alcohol is removed as described above, the physical properties of an ester-based composition to be manufactured may be uniform and excellent.

Typically, it is desirable that the separation column is operated continuously in terms of production management, and to this end, the reaction products discharged from each reactor may temporarily stay in a piece of equipment such as a tank before being injected into the separation column. The reaction products including the unreacted alcohol may stay in the equipment for about 0.1-10 hours, and the size of the equipment is not limited as long as the reaction products are stably and continuously supplied to the separation column.

Catalyst Addition Step (S1-1 or S1-2)

The manufacturing method of the present invention may further include a step S1-1 of adding a catalyst to the reaction mixture between the step S1 and the step S2, or a step S1-2 of adding a catalyst to a polycarboxylic acid and a first alcohol having 3 to 10 alkyl carbon atoms before the step S1.

In the esterification reaction of the first alcohol and the carboxylic acid, a catalyst may be used, and when a catalyst is used, there is an advantage in that the reaction may be completed faster. The catalyst may be injected to a mixture of a polycarboxylic acid and a first alcohol, or to each of a polycarboxylic acid and a first alcohol before a mixture thereof is prepared. Particularly, it is preferable that the catalyst is added directly to the first alcohol in terms of the efficiency of the entire process.

The catalyst used in the manufacturing method of the present invention may be one or more selected from an acid catalyst such as sulfuric acid, hydrochloric acid, phosphoric acid, nitric acid, paratoluenesulfonic acid, methanesulfonic acid, ethanesulfonic acid, propanesulfonic acid, butanesulfonic acid, and alkyl sulfuric acid, a metal salt such as aluminum lactate, lithium fluoride, potassium chloride, cesium chloride, calcium chloride, iron chloride, and phosphoric acid, a metal oxide such as heteropoly acid, a natural/synthetic zeolite, a cation and anion exchange resin, and an organic metal such as tetraalkyl titanate and a polymer thereof, and may preferably be tetraalkyl titanate. As the tetraalkyl titanate, TiPT, TnBT, TEHT, or the like may be used, and it is preferable to use tetraalkyl titanate having an alkyl group same as the alkyl group of the first alcohol having 3 to 10 alkyl carbon atoms as a ligand. When a catalyst having the same alkyl group as a ligand is used, it is preferable because catalyst by-products which may be generated in a subsequent process are controlled or not generated.

The amount of a catalyst to be used may vary depending on the kind of the catalyst. In one example, a homogeneous catalyst may be used in an amount range of 0.001-5 wt %, 0.001-4 wt %, 0.01-3 wt %, or 0.01-2 wt % based on 100 wt % of the reaction mixture, and a heterogeneous catalyst may be used in an amount range of 5-200 wt %, 5-150 wt %, 10-150 wt %, or 20-150 wt % based on the total weight of the reaction mixture.

Trans-Reaction Step (S4)

The manufacturing method of the present invention may further include a step S4 of injecting a second alcohol having 3 to 10 alkyl carbon atoms into the reaction products from which the unreacted alcohol is removed to perform a trans-esterification reaction, wherein the second alcohol injected herein is different from the first alcohol injected in the step S1.

Through the step S4, it is possible to manufacture a composition including two or more types of ester compounds. Those skilled in the art may select suitable alcohol according to the type of an ester compound to be included in the composition and perform a trans-esterification reaction. It is preferable that the step S4 is performed after the removal of unreacted alcohol. When the step S4 is performed before the removal of the unreacted alcohol, a trans-esterification reaction with newly injected second alcohol may not be easily performed due to the remaining unreacted alcohol, and even the reaction is performed to a certain degree, the alcohol content is too high to deteriorate the efficiency of the reaction. Therefore, it is preferable that the amount of the unreacted alcohol included in the reaction products before the trans-esterification reaction is 10% or less.

DESCRIPTION OF THE REFERENCE NUMERALS OR SYMBOLS

1: Mixer
11: Injection path of polycarboxylic acid
12: Injection path of first alcohol
13: Injection path of catalyst
2: Supply control unit
3: Reaction unit
31 to 3N: Each batch reactor (total of N reactors)
4: Separation unit
41: Movement path of ester-based composition from which unreacted alcohol is removed
42: Movement path of removed unreacted alcohol
5: Trans-reaction unit
51: Injection path of second alcohol different from first alcohol injected into 12
52: Movement path of ester-based composition which has been gone through trans-esterification reaction
92: Second recovery alcohol stream
93: Wastewater stream

The invention claimed is:

1. A system for manufacturing an ester-based composition, the system comprising:
   a mixer in which a reaction mixture of a polycarboxylic acid and a first alcohol having 3 to 10 alkyl carbon atoms is formed, wherein the mixer comprises a polycarboxylic acid injection path and a first alcohol injection path;
   a reaction unit provided with N number of batch reactors connected in parallel in which an esterification reaction of the reaction mixture is performed, an inlet line for receiving the reaction mixture from the mixer, and an outlet line for discharging reaction products from the N number of batch reactors;
   a supply control unit for controlling the injection amount and the injection path of the reaction mixture such that the reaction mixture is sequentially supplied to the N number of batch reactors from the mixer to allow the reaction to be sequentially completed, wherein the supply control unit is disposed between the mixer and the reaction unit; and
   a separation unit for receiving the reaction products through the outlet line of the reaction unit and removing unreacted alcohol therefrom.

2. The system of claim 1, further comprising a trans-reaction unit for performing a trans-esterification reaction by adding a second alcohol having 3 to 10 alkyl carbon atoms to the reaction products from which the unreacted alcohol has been removed, wherein the second alcohol injected from the trans-reaction unit is different from the first alcohol injected from the mixer.

3. The system of claim 1, wherein at least one batch reactor a mong the N number of batch reactors comprises a gas-liquid separation column connected to an upper portion of the batch reactor and separating alcohol and water discharged through the upper portion of the batch reactor, a condenser for cooling a gas discharged through an upper line of the gas-liquid separation column, and a decanter for separating a liquid discharged through a lower line of the gas-liquid separation column and a liquid condensed in the condenser into different layers and recirculating the alcohol into the batch reactor.

4. The system of claim 1, wherein the supply control unit controls one or more of the injection path and the injection flow rate of the reaction mixture to be changed according a predetermined time interval.

5. The system of claim 4, wherein the time interval is 50% to 150% of a value obtained by dividing the reaction duration in one batch reactor by N.

6. A system for manufacturing an ester-based composition, the system comprising:
- a mixer in which a reaction mixture of a polycarboxylic acid and a first alcohol having 3 to 10 alkyl carbon atoms is formed, wherein the mixer comprises a polycarboxylic acid injection path and a first alcohol injection path;
- a reaction unit provided with N number of batch reactors connected in parallel in which an esterification reaction of the reaction mixture is performed, an inlet line for receiving the reaction mixture from the mixer, and an outlet line for discharging reaction products from the N number of batch reactors;
- a supply control unit for controlling the injection amount and the injection path of the reaction mixture such that the reaction mixture is sequentially supplied to the N number of batch reactors from the mixer to allow the reaction to be sequentially completed, wherein the supply control unit is disposed between the mixer and the reaction unit; and
- a separation unit for receiving the reaction products through the outlet line of the reaction unit and removing unreacted alcohol therefrom, wherein the polycarboxylic acid is one or more selected from the group consisting of a dicarboxylic acid, a tricarboxylic acid, and a tetracarboxylic acid.

7. The system of claim 6, wherein
the dicarboxylic acid is one or more selected from the group consisting of a linear dicarboxylic acid having 2 to 10 carbon atoms, a terephthalic acid, a phthalic acid, an isophthalic acid, a cyclohexane dicarboxylic acid, an anhydride thereof, and a derivative thereof,
the tricarboxylic acid is one or more selected from the group consisting of a citric acid, a trimellitate acid, a cyclohexane tricarboxylic acid, an anhydride thereof, and a derivative thereof, and
the tetracarboxylic acid is one or more selected from the group consisting of a benzenetetracarboxylic acid, a furantetracarboxylic acid, a cyclohexane tetracarboxylic acid, a tetrahydrofuran tetracarboxylic acid, an anhydride thereof, and a derivative thereof.

* * * * *